United States Patent
Ramanathan et al.

(10) Patent No.: US 11,774,443 B2
(45) Date of Patent: Oct. 3, 2023

(54) DRY-DOWN PROCESSES FOR DYE-CONJUGATED REAGENTS

(71) Applicant: Beckman Coulter, Inc., Brea, CA (US)

(72) Inventors: Sridhar Ramanathan, Bangalore (IN); Badri Narayanan Natarajan, Bangalore (IN)

(73) Assignee: Beckman Coulter, Inc., Brea, CA (US)

( * ) Notice: Subject to any disclaimer, the term of this patent is extended or adjusted under 35 U.S.C. 154(b) by 0 days.

(21) Appl. No.: 17/533,425

(22) Filed: Nov. 23, 2021

(65) Prior Publication Data
US 2022/0091108 A1    Mar. 24, 2022

Related U.S. Application Data (63) Continuation of application No. 16/311,589, filed as application No. PCT/US2017/038179 on Jun. 19, 2017, now Pat. No. 11,249,075.

(30) Foreign Application Priority Data

Jun. 20, 2016   (IN) .............................. 201611021054

(51) Int. Cl.
*C12N 15/10* (2006.01)
*B01L 3/00* (2006.01)
(Continued)

(52) U.S. Cl.
CPC ............ *G01N 33/532* (2013.01); *B01L 3/508* (2013.01); *B01L 3/52* (2013.01); *C12Q 1/6876* (2013.01);
(Continued)

(58) Field of Classification Search
CPC ........ G01N 33/532; G01N 1/30; G01N 15/14; G01N 2015/1006; B01L 3/508;
(Continued)

(56) References Cited

U.S. PATENT DOCUMENTS

2005/0094807 A1* 5/2005 Silzel .................. C12Q 1/6837
380/46
2006/0263907 A1* 11/2006 Zweig ................. G01N 33/588
436/524
(Continued)

FOREIGN PATENT DOCUMENTS

| CN | 1245561 | 2/2000 |
|----|---------|--------|
| CN | 101998992 | 3/2011 |

(Continued)

OTHER PUBLICATIONS

U.S. Appl. No. 16/311,589, filed Dec. 19, 2018, Dry-Down Processes for Dye-Conjugated Reagents.
(Continued)

*Primary Examiner* — Jennifer Wecker
*Assistant Examiner* — Oyeleye Alexander Alabi
(74) *Attorney, Agent, or Firm* — Merchant and Gould, PC (57) ABSTRACT

The method involves drying down dye-conjugated reagents in separate locations in a reaction vessel so that the dyes don't non-specifically interact with each other during drying. This invention thus improves multiplex binding assays by eliminating erroneous results caused by dyes' being non-specifically attached to each other when dried down together.

20 Claims, 3 Drawing Sheets

(51) Int. Cl.
| | |
|---|---|
| G01N 21/3504 | (2014.01) |
| G01N 33/00 | (2006.01) |
| G01N 33/574 | (2006.01) |
| G01N 21/64 | (2006.01) |
| A61K 45/06 | (2006.01) |
| G01N 21/35 | (2014.01) |
| G01N 33/532 | (2006.01) |
| G01N 1/30 | (2006.01) |
| C12Q 1/6876 | (2018.01) |
| G01N 15/14 | (2006.01) |
| G01N 15/10 | (2006.01) |

(52) U.S. Cl.
CPC .............. *G01N 1/30* (2013.01); *G01N 15/14* (2013.01); *B01L 2200/16* (2013.01); *B01L 2300/069* (2013.01); *B01L 2300/0829* (2013.01); *C12Q 2600/16* (2013.01); *G01N 2015/1006* (2013.01)

(58) Field of Classification Search
CPC .. B01L 3/52; B01L 2200/16; B01L 2300/069; B01L 2300/0829; C12Q 1/6876; C12Q 2600/16
See application file for complete search history.

(56) References Cited

U.S. PATENT DOCUMENTS

| | | | |
|---|---|---|---|
| 2009/0246782 | A1 | 10/2009 | Kelso et al. |
| 2011/0171738 | A1 | 7/2011 | Aoki et al. |
| 2011/0288284 | A1* | 11/2011 | Makarov .............. C12Q 1/6846 536/23.1 |
| 2017/0307600 | A1* | 10/2017 | Sharkey .................. B01L 3/523 |
| 2019/0242882 | A1 | 8/2019 | Ramanathan et al. |

FOREIGN PATENT DOCUMENTS

| | | |
|---|---|---|
| CN | 104704363 | 6/2015 |
| CN | 109562379 | 4/2019 |
| EP | 0465715 A1 * | 1/1991 |
| HK | 40006982 | 5/2020 |
| WO | 2015175861 | 11/2015 |
| WO | 2017222998 | 12/2017 |

OTHER PUBLICATIONS

"International Application Serial No. PCT US2017 038179, International Search Report dated Sep. 26, 2017", 4 pgs.

"International Application Serial No. PCT US2017 038179, Written Opinion dated Sep. 26, 2017", 7 pgs.

"International Application Serial No. PCT US2017 038179, International Preliminary Report on Patentability dated Jan. 3, 2019", 9 pgs.

"ReaPan 34845", Anonymous: XP55407174, Retrieved from the Internet:http: www.demo.reametrix.comjdownload QMS Product Inserts ReaPan34845.pdf, [retrieved on Sep. 14, 2017], (Jan. 30, 2013), 1-2.

"U.S. Appl. No. 16/311,589, Preliminary Amendment filed Dec. 19, 2018", 5 pgs.

"Chinese Application Serial No. 201780047903.7, Office Action dated Nov. 26, 2020", with English translation, 22 pages.

"Application Serial No. 16 311,589, Non Final Office Action dated Feb. 11, 2021", 14 pgs.

"U.S. Appl. No. 16/311,589, Response filed Mar. 4, 2021 to Non Final Office Action dated Feb. 11, 2021", 12 pgs.

"U.S. Appl. No. 16/311,589, Final Office Action dated Apr. 13, 2021", 31 pgs.

"Chinese Application Serial No. 201780047903.7, Response filed Apr. 9, 2021 to Office Action dated Nov. 26, 2020", with English claims, 15 pages.

"U.S. Appl. No. 16/311,589, Response filed May 26, 2021 to Final Office Action dated Apr. 13, 2021", 11 pgs.

"U.S. Appl. No. 16/311,589, Advisory Action dated Jun. 4, 2021", 4 pgs.

"U.S. Appl. No. 16/311,589, Non Final Office Action dated Jun. 14, 2021", 31 pgs.

"Chinese Application Serial No. 201780047903.7, Office Action dated Jul. 26, 2021", with English translation, 25 pages.

"U.S. Appl. No. 16/311,589, Response filed Aug. 31, 2021 to Non Final Office Action dated Jun. 14, 2021", 12 pgs.

"U.S. Appl. No. 16/311,589, Notice of Allowance dated Oct. 27, 2021", 9 pgs.

"Indian Application Serial No. 201947002294, First Examination Report dated Nov. 1, 2021", with English translation, 5 pages.

Bergeron, M., "Evaluation of a dry format reagent alternative for CD4 T-cell enumeration for the FACSCount system: A report on a Moroccan-Canadian study", Cytometry Part B: Clinical Cytometry, vol. 78B. (Oct. 21, 2009). XP055406401., (Oct. 21, 2009), 6 pages.

Jung, W., "Point-of-care testing (POCT) diagnostic systems using microfluidic lab-on-a-chip technologies", Microelectron, Engineer vol. 132, (Oct. 8, 2014). XP029100128, (Oct. 8, 2014), 12 pages.

Thakar, M., "CD4 estimating reagents in dry format are compatible with conventional flow cytometer; FACSCalibur for estimation of absolute CD4 count and percentages", Indian J. Med. Res .vol. 137. No. 2, (Feb. 2013), XP55406800., (Feb. 2013), 346-355.

* cited by examiner

DRY-DOWN PROCESSES FOR DYE-CONJUGATED REAGENTS

RELATIONS TO OTHER APPLICATIONS

This application is a continuation of U.S. application Ser. No. 16/311,589, filed Dec. 19, 2018, now U.S. Pat. No. 11,249,075, which application is a U.S. National Stage Filing under 35 U.S.C. 371 from International Application No. PCT/US2017/038179, filed on Jun. 19, 2017, and published as WO 2017/222998 on Dec. 28, 2017, which application claims benefit of the Indian Application No. 201611021054, filed Jun. 20, 2016, the entire content of which are hereby incorporated by reference for all purposes.

FIELD OF THE INVENTION

This invention relates to methods, articles and compositions for the detection and analysis of target analytes in a liquid sample.

BACKGROUND OF THE INVENTION

Biological assays are important for detecting or quantifying certain molecules or analytes of interest. These analytes may be important for medical diagnosis or for some other research purposes. The assay can be an enzymatic or a binding assay, such as an immunoassay. Assays typically require a labeled reagent to visualize the target or analyte of interest. When using a label, it is important that the label remains associated with a single reagent to accurately measure the specific target.

Biological assays, such as immunoassays, typically use biological reagents, such as antibodies or other proteins to detect and optionally quantitate the target analyte. Binding of the analyte to the biological reagent can be detected and measured using a label attached to the reagent, such as a fluorescent dye, non-fluorescent dye, or an enzyme.

Multiplexed assays allow simultaneous detection of multiple analytes in a single assay. For immunoassays, multiplexed assays involve a cocktail of antibodies, each labeled with a different dye. Each antibody binds to a specific analyte in the sample. In this way, the different analytes can be differentiated and quantitated based on the different dyes.

For convenience, multiplex assay reagents can be supplied as a premixed cocktail of individual binding molecules, such as antibodies. Other reaction components may be included in the cocktail, such as buffer, salt, surfactant, etc. Most convenient is a cocktail containing all necessary components (a unitary assay reagent). In this case, the assay can be performed by simply adding sample to a reaction vessel containing the cocktail.

It is convenient to provide a stable assay reagent, particularly a reagent that is stable at room temperature. This allows shipment and storage of the reagent without refrigeration. This is especially important for assays performed in rural areas where resources, including electricity, may be limited.

In prior art, stable reagents are provided by drying down aqueous solutions of the reagent, or by lyophilization. But a problem exists with some labeled reagents. These reagents become cross-linked during the drying process. They remain cross-linked after resuspension in liquid solution, so that the labels are no longer associated with individual molecules, causing erroneous results. This can be especially problematic, for example, in the field of flow cytometry, in which a plurality of polymeric dyes are used to create 10 or more fluorescent channels by using only one wavelength for excitation. The chemical nature of these polymeric dyes, however, prevents the storage of formulations of multiple dyes in the same solution. It has been observed that the polymeric entities bind with each other (potentially a hydrophobic bond) in solution. This results in either erroneous compensation settings or anomalous cell populations that cannot exist in reality. Hence antibodies conjugated to these dyes are typically stored separately and formulated prior to the experiment. When running multi-parameter, multisite studies, this introduces additional variability. Further, since reagents formulated cannot be stored for a long period of time, it can also result in wastage.

BRIEF SUMMARY OF THE INVENTION

This invention provides substrates comprising dry reactant compositions and methods to produce them. The compositions comprise stable, multiple labeled reagents that do not become cross-linked during the drying process. The stable reagent can be used to improve multiplex binding assays.

In a first aspect, the invention provides a reaction vessel comprising a body containing a first dry reactant spot disposed on a first substrate. For purposes of this disclosure, a spot can be of any shape and be present on the substrate in any format. The first dry reactant spot comprises a first binding partner conjugated to a first polymer dye. The reaction vessel body additionally contains a second dry reactant spot disposed on a second substrate. The second dry reactant spot comprises a second binding partner conjugated to a second polymer dye. The reaction vessel is configured to receive a liquid sample, which contacts the first and second dry reactant spots. Such contact results in dissolution of the first and second binding partners to form a liquid reaction mixture comprising the first binding partner and the second binding partner in the reaction vessel. In some embodiments, the reaction vessel comprises a body containing a plurality of, e.g., two, three, or more, dry reactant spots, each disposed on a different substrate and comprising a different binding partner conjugated to a different polymer dye. The reaction vessel is configured to receive a liquid sample, which contacts the plurality of dry reactant spots and such contact results in dissolution of different binding partners in respective reactant spots to form a liquid reaction mixture comprising the different binding partners.

In one embodiment, at least one of the first substrate and the second substrate is a membrane or a bead. In one embodiment, at least one of the first substrate and the second substrate is an inside surface of the body of the reaction vessel. In one embodiment, the second substrate is layered above the first substrate. In one embodiment, at least one of the first substrate and the second substrate is bonded to an inside surface of the body of the reaction vessel.

In one embodiment, at least one of the first dry reactant spot and the second dry reactant spot is fixed to the substrate. In one embodiment, at least one of the first dry reactant spot and the second dry reactant spot is in the form of a film, wherein the film fixes the first or second binding partner to the substrate.

In one embodiment, the first binding partner conjugated to the first dye in the first spot and the second binding partner conjugated to the second dye in the second spot are stable at room temperature for at least one month.

In one embodiment, the first binding partner conjugated to the first dye in the first spot and the second binding partner conjugated to the second dye in the second spot are stable at room temperature for at least one year.

In one embodiment, the reaction vessel is a well of a microtiter plate.

In a second aspect, the invention provides a reaction vessel comprising a body containing a first dry reactant spot disposed on a substrate. The first dry reactant spot comprises a first binding partner conjugated to a first dye. The reaction vessel body additionally contains a second dry reactant spot disposed on the substrate and the second dry reactant spot comprises a second binding partner conjugated to a second dye. The first dry reactant spot and the second dry reactant spot are at least substantially physically separated on the substrate. The reaction vessel is configured to receive a liquid sample, which contacts the first and second dry reactant spots. Such contact results in dissolution of the first and second binding partners to form a liquid reaction mixture comprising the first binding partner and the second binding partner in the reaction vessel.

In one embodiment, the first dry reactant spot and the second dry reactant spot do not overlap. In one embodiment, the first dry reactant spot and the second dry reactant spot partially overlap. In one embodiment, the reaction vessel further comprises a divider disposed between the first dry reactant spot and the second dry reactant spot. In one embodiment, the divider is configured to separate the first binding partner from the second binding partner in the reaction vessel before receiving the liquid sample.

In one embodiment, the substrate is an inside surface of the body of the reaction vessel. In one embodiment, the substrate is a membrane or a bead.

In one embodiment, at least one of the first dye and the second dye is a polymer dye.

In one embodiment, at least one of the first dry reactant spot and the second dry reactant spot is fixed to the substrate. In one embodiment, at least one of the first dry reactant spot and the second dry reactant spot is in the form of a film, wherein the film fixes the first or second binding partner to the substrate.

In one embodiment, the first binding partner conjugated to the first dye in the first spot and the second binding partner conjugated to the second dye in the second spot are stable at room temperature for at least one month.

In one embodiment, the first binding partner conjugated to the first dye in the first spot and the second binding partner conjugated to the second dye in the second spot are stable at room temperature for at least one year.

In one embodiment, the reaction vessel is a well of a microtiter plate.

In a third aspect, the invention provides a method of preparing two or more dry reactant spots. The method comprises: dispensing a first reactant including a first binding partner conjugated to a first dye in liquid phase onto a first substrate, wherein the first dye is a polymer dye. The method further comprises dispensing a second reactant including a second binding partner conjugated to a second dye in liquid phase onto a second substrate, wherein the second dye is a polymer dye. The method further comprises drying the first reactant and the second reactant in liquid phase to form a first dry reactant spot on the first substrate and a second dry reactant spot on the second substrate.

In one embodiment, the method further comprises placing the first substrate and the second substrate inside a reaction vessel. In one embodiment, at least one of the first substrate and the second substrate is a membrane. In one embodiment, the method further comprises bonding at least one of the first substrate and the second substrate to an inside surface of a reaction vessel.

In one embodiment, at least one of the first substrate and the second substrate is a bead. In one embodiment, at least one of the first substrate and the second substrate is an inside surface of a reaction vessel. In one embodiment, at least one of the first dye and the second dye is a polymer dye. In one embodiment, the first reactant and the second reactant are dried simultaneously.

In a fourth aspect, the invention provides a method of preparing two or more dry reactant spots. The method comprises drying a first reactant in liquid phase onto a substrate to form a first dry reactant spot; and drying a second reactant in liquid phase onto the substrate to form a second dry reactant spot. The first reactant including a first binding partner conjugated to a first dye the second reactant including a second binding partner conjugated to a second dye. The first dry reactant spot and the second dry reactant spot are at least substantially physically separated on the substrate and at least one of the first dye and second dye is a polymer dye.

In one embodiment, the method further comprises maintaining physical separation of the first reactant and the second reactant during drying, such that the first dry reactant spot and the second dry reactant spot do not overlap. In one embodiment, the method further comprises placing the substrate inside a reaction vessel. In one embodiment, the first reactant and the second reactant are dried simultaneously.

In one embodiment, the substrate is a membrane or a bead. In one embodiment, the substrate is an inside surface of a reaction vessel. In one embodiment, the method further comprises bonding the substrate to an inside surface of a reaction vessel.

DEFINITIONS

As used herein, the following terms and variations thereof have the meanings given below, unless a different meaning is clearly intended by the context in which such term is used.

"Analyte" refers to a molecule, compound, or other component in a sample. Analytes include but are not limited to peptides, proteins, polynucleotides, organic molecules, sugars and other carbohydrates, and lipids.

"Antibody" refers to an immunoglobulin protein or to a fragment or derivative thereof which specifically binds to an analyte. Antibodies include various classes and isotypes of immunoglobulins, such as IgA, IgD, IgE, IgG1, IgG2a, IgG2b, IgG3, and IgM. Antibody fragments include molecules such as Fab, scFv, F(ab')2, and Fab' molecules. Antibody derivatives include antibodies or fragments thereof having additions or substitutions, such as chimeric antibodies. Antibodies can be derived from human or animal sources, from hybridomas, through recombinant methods, or in any other way known to the art.

"Binding partner" refers to a molecule capable of specially binding an analyte. A binding partner can be any of a number of different types of molecules, including an antibody or other protein, peptide, polysaccharide, lipid, a nucleic acid or nucleic-acid analog, such as an oligonucleotide or PNA (peptide nucleic acids).

"Labeled binding partner" refers to a binding partner that is conjugated to a dye.

"Reactant solution" refers to solution comprising the labeled binding partner. In some embodiments, besides the labeled binding partner, a reactant solution further comprise stabilizers, salt, buffer, surfactants, and/or other reagents.

"Dry reactant spot" refers to a spot formed on the substrate of a reaction vessel by drying the reactant deposited thereon.

"At least substantially physically separated" refers to the spatial relationship between two dry reactant spots, which typically do not touch each other or may partially overlap such that erroneous results resulting from cross-linking of dyes are substantially reduced or eliminated.

"Multiplexing" herein refers to an assay or other analytical method in which multiple analytes can be assayed simultaneously.

DETAILED DESCRIPTION

Overview

The invention provides methods to minimize erroneous results in binding assays that may be caused by dyes' being non-specifically attached ("sticking") to each other when dried down together. The non-specific attachment is often a problem for assays using regents labeled with polymeric dyes. The present invention solves the problem by drying down dye-conjugated reagents in separate locations on one or more substrates so that the dyes do not interact during drying. The dye-conjugated reagents (labeled binding partners) can independently bind to target analytes in the liquid sample to be analyzed and erroneous results arising from cross-linking are substantially reduced or eliminated.

Specific Embodiments

Reaction Vessel

A reaction vessel disclosed herein can be any container where reactions between the binding partners and the target analytes can occur. For example, a reaction vessel can be a tube, a plate, a well of a microtiter plate, a chamber, and a slide. In a preferred embodiment, a reaction vessel has a lid or cap such that the binding reaction can occur in a closed environment.

Substrate

A reaction vessel comprises one or more substrates. The substrate can be any suitable surface, including but not limited to, plastic, nitrocellulose, cellulose acetate, and glass. In some embodiments, the substrate is a membrane. The substrate can be the inside surface of the body of a reaction vessel, e.g., a plastic tube or well of a microtiter plate. The substrate can also be a bead. In some embodiments, at least one of the substrates receiving the labeled binding partners (e.g., a membrane) is bonded to an inside surface of the body of the reaction vessel. In some embodiments, the membrane substrate is a sheet or roll, which makes it easier to deposit the solutions and easier to dry. In some embodiments, the membrane can be cut to separate individual dried reactant spots. In some embodiments, the cut membrane is simply dropped into the reaction vessel. In some preferred embodiments, the cut membranes are bonded to the surface of the reaction vessel, so that the spots do not escape the vessel when liquid is pipetting into or out of the reaction vessel.

Liquid Sample

The reaction vessel is configured to receive a liquid sample. Liquid samples used in the invention typically comprise target analytes obtained as or dispersed in a predominantly aqueous medium. Samples can be any source of biological material which comprises polynucleotides that can be obtained from a living organism, directly or indirectly. Samples can include, e.g., cells, tissue or fluid, and the deposits left by that organism, including viruses, mycoplasma, and fossils. The sample may comprise a target analyte prepared through synthetic means, in whole or in part. Non-limiting examples of the sample include blood, urine, semen, milk, sputum, mucus, a buccal swab, a vaginal swab, a rectal swab, an aspirate, a needle biopsy, a section of tissue obtained for example by surgery or autopsy, plasma, serum, spinal fluid, lymph fluid, the external secretions of the skin, respiratory, intestinal, and genitourinary tracts, tears, saliva, tumors, organs, samples of in vitro cell culture constituents (including but not limited to conditioned medium resulting from the growth of cells in cell culture medium, putatively virally infected cells, recombinant cells, and cell components).

Target Analytes

The present invention is designed to detect the presence, and in some cases the quantity of specific target analytes. Target analytes disclosed herein refer to a target molecule to be detected, for example, peptides, proteins, polynucleotides, organic molecules, sugars and other carbohydrates, and lipids. It is an important aspect of the invention that the target analyte are comprised in a liquid sample and are accessible, or made accessible at some point, to bind analyte-specific binding partners of the instant invention.

Target analytes can be present in beads, or present and accessible on the surface of cells. Illustrative examples of useful analytes include, but are not limited to, the following: 1) specific cell surface macromolecules and antigens (including hormones, protein complexes, and molecules recognized by cell receptors) and 2) cellular proteins, DNA or RNA in permeablized cells including abnormal DNA or RNA sequences or abnormal amounts of certain messenger RNA. Detection of these analytes is particularly useful in situations where they are contained in and/or are identifiers of rare cells such as are found in the early stages of a variety of cancers.

Binding Partner

The binding partners disclosed herein bind specifically to target analytes. A number of different types of binding partners can be used in the present system and methods. In one embodiment, the binding partner is an antibody. Antibodies used to bind a particular analyte are preferably monoclonal, and thus are directed against a single epitope of an analyte. Monoclonal antibodies can be prepared using techniques known to the art, and are typically prepared through the creation of a hybridoma using a B-cell line that produces an antibody with desired binding characteristics. Antibodies directed against a single epitope can also be generated in other ways, such as through recombinant methods. In some embodiments, polyclonal antibodies can be used as specific binding partners in the present system and methods. For example, a binding partner can be polyclonal antibodies raised against epitopes of the analyte. Polyclonal antibodies can be prepared in ways known to the art, such as by immunizing a host and collecting plasma or serum from that host. Antibody fragments, which retain their specific binding characteristics, can also be used as specific binding partners in the present invention, including fragments lacking the Fc portion of an antibody, e.g., Fab, Fab' and F(ab')2 fragments. F(ab')2 fragments can be produced by methods known to the art, e.g., by cleaving a monoclonal antibody with proteolytic enzymes such as papain and pepsin. Fab' fragments can be produced by reductive cleavage of F(ab')2 fragments with agents such as dithiothreitol or mercaptoethanol. Antibody fragments can alternatively be produced using recombinant methods, such as through the use of a phage display library.

Binding partners other than antibodies or antibody fragments or derivatives can also be used in the present system and methods. For example, binding partners may be nucleic acids or nucleic-acid analogs, such as oligonucleotides or PNA probes. In one embodiment, aptamers can be used as specific binding partners. Aptamers are single-stranded DNA or RNA (ssDNA or ssRNA) molecules that can bind to pre-selected targets including proteins and peptides with high affinity and specificity. Other binding partner that can bind to target analyte to form pairs of receptor-ligand, enzyme-substrate, enzyme-inhibitor, and enzyme-cofactor pairs can also be used. Specific examples of such specific binding partner pairs include carbohydrate and lectin, biotin and avidin or streptavidin, folic acid and folate binding protein, vitamin B12 and intrinsic factor, Protein A and immunoglobulin, and Protein G and immunoglobulin. Also included are binding partners that form a covalent bond with the target analytes.

Dye

A dye is a moiety that provides a detectable signal, which can be attached to or incorporated into a binding partner, either directly or indirectly. A dye used in the invention can be colored, fluorescent, or luminescent, and is typically detected by detector, e.g., a flow cytometer. Fluorescent dyes can be monomeric or polymeric. Non-limiting examples of monomeric dyes include fluorescein, rhodamine, and cyanine.

Polymeric dyes are particularly useful for analysis of chemical and biological targets. They are highly responsive optical reporters and efficient light absorbers, by virtue of the multiple chromophores they comprise. Examples of polymeric dyes include, but are not limited to, conjugated polymers having repeat units of chromophore, aggregates of conjugated molecules, luminescent dyes attached via side chains to saturated polymers, semiconductor quantum dots and dendritic structures.

Polymeric and monomeric dyes disclosed in U.S. Pat. Nos. 7,214,489, 8,354,239, 8,575,303 can also be used for the present invention.

Labeled Binding Partner

Dyes can be conjugated to binding partners by various linking chemistry between reactive pairs located in the binding partners and the labels. The reactive pairs can include, but not limited to, maleimide/thiol, succimidylester (NHS ester)/amine, azide chemistry, carboxy/EDC (1-Ethyl-3-[3-dimethylaminopropyl]carbodiimide Hydrochloride)/amine, amine/Sulfo-SMCC (Sulfosuccinimidyl 4-[N-maleimidom ethyl]cyclohexane-1-carboxylate)/thiol, and amine/BMPH (N-[~-Maleimidopropionic acid]hydrazide.TFA)/thiol. Methods for performing the conjugation are well known in the art. Commercial kits for performing the conjugation are also readily available, e.g., from Innova biosciences (Cambridge, UK), Novus Biologicals (Littleton, Colo.), Thermo Fisher Scientific (Waltham, Mass.).

Reactant Solutions

The reactant solutions comprising the labeled binding partners are not a critical aspect of the invention. Such solutions will typically be an aqueous solution comprising stabilizers, salts, buffers, surfactants, and/or other reagents well known to those of skill in the art, Stabilizers used in the solutions of the invention can be proteins (e.g., bovine serum albumin, gelatin, milk), carbohydrates (e.g., trehalose, dextrose, sucrose), or organic polymers (e.g., polyethylene glycol and polyvinyl pyrrolidone). In some embodiments, the stabilizers can facilitate the attachment of the dry reactant spots to the substrate, so that the spots remain at the bottom of the tube and will not be blown away or stick to the cap when the reaction vessel is opened.

Depositing and Drying Reactant Solutions onto the Substrate

A reactant solution comprising molecules of a labeled binding partner is deposited on a desired location on the substrate. The volume of the reactant solution being deposited can vary. In some embodiments, the volume is 1-20 µl. In some embodiment, the volume is 2-10 µl. In a preferred element, the volume is 2-5 µl.

The substrate with the deposited reactant solution is then dried down in a non-frozen form (i.e. not lyophilized) until the reactant is substantially free of water and forms a dry spot. Suitable temperatures and atmospheric pressures for the drying process vary depending on the properties of the binding partners.

Labeled binding partners having different labels are prevented from interacting with each other by being kept at least substantially physically separated. This goal can be achieved in a variety of ways. For example, reactant solutions comprising different labeled binding partners can be dried on different locations on the same substrate (e.g., the inside of a reaction vessel). In some embodiments, reactant solutions comprising different labeled binding partners are dried onto different substrates and placed in the same reaction vessel. In some embodiments, the reaction vessel contains multiple layers of substrate (e.g., membranes), each comprising a different reactant. In some embodiments, dividers are disposed between the different locations where the reactant solutions are deposited on the same substrate. The divider is configured to separate a first labeled binding partner from a second labeled binding partner on the substrate (e.g., the inner wall of a reaction vessel) before receiving the liquid sample. The divider can be in the form of a well, a dimple, or some form of protrusion from the surface and it can be used to maintain the separation of the reactants during drying.

Different reactant solutions can be deposited and dried simultaneously or sequentially. When two reactant solutions are deposited and dried sequentially, it is not necessary for the first reactant solution to be completely dry before depositing a second reactant solution.

The Dry Reactant Spots

Dry reactant spots can take any geometric shapes, for example, round or oval. The sizes of the dry reactant spots can vary, depending on various factors, e.g., the volume of the reactant being deposited on the substrate and the properties of the substrate. In some embodiments, the diameter of the dry reactant spots is 1 mm-8 mm, or 1 mm-5 mm. Typically, a 2-5 ul of reactant solution form a dry reactant spot with a diameter of 2 mm.

Dry reactant spots are generally non-overlapping, but some overlap may be allowed, as long as it doesn't lead to significant cross-linking of the dyes. In some embodiments, the dry reactant spots are physically separated. In some embodiments, they partially overlap. In some embodiments they are separated such that the centers between any two dry reactant spots are at least 10 mm, at least 50 mm, or at least 100 mm, apart. It is within the skill of one of skill in the art to determine the acceptable extent of overlapping or suitable degree of separation between the dry reactant spots for the purpose of the invention.

In some embodiments, a second dry reactant spot is positioned above the first dry reactant spot, for example, the second spot is formed in a layer of substrate positioned above the layer of substrate where the first one is formed.

In some embodiments, at least one of the reactant spots is in the form of a film, in which the binding partner is fixed to the substrate. Fixing to the substrate could entail forming a non-chemical bond between the binding partner and the substrate that allows the binding partner to be retained on the substrate over a period of time. This is typically done by forming a thin film on the substrate that is then retained on the substrate due to physical adhesive forces.

Other assay components (buffer, salt, surfactant, lysing, permeabilizing, or fixative reagents) may also deposited and dried onto the same substrate as the one having the dry reactant spots. These assay components can be deposited as separate spots or combined with the labeled binding partners. Spots of these assay components can overlap or even superimpose on the dry reactant spots, because they do not comprise dyes and thus do not interact with the dyes in the labeled binding partners.

Stability of the Labeled Binding Partners

Preserving binding partners in dry reactant spots in the body of a vessel significantly increase their stability. Stability of a binding partner is measured by its ability to bind its target analyte after being in storage for a period of time. Unlike cocktails of binding partners preserved in solution, which have relatively short shelf-life, the binding partners preserved in separate dry reactant spots in the reaction vessel are stable over a long period of time. In some cases, these labeled binding partners showed no measurable loss of activity in binding their target analytes for after being stored at 42° C. for at least 2 years. For the purpose of this invention, the labeled binding partners in their respective dry reactant spots are stable at room temperature for at least one month, or at least six months, or at least a year.

Performing a Multiplex Binding Assay Using the Reaction Vessels

To perform a multiplex binding assay, a suitable amount of liquid sample comprising target analytes is added to the reaction vessel containing two or more dry reactant spots, prepared as described above. The liquid sample, upon contacting the spots, dissolves the labeled binding partners to form a reaction mixture. The target analytes from the liquid sample bind to their respective binding partners. The binding can be detected using a device detecting the dyes conjugated to the binding partners. The present invention thus can be used to improve many multiplex assay platforms, including but not limited to, flow cytometry, immunoassay, Western blot, PCR, or binding assays using labeled probes or proteins.

EXAMPLES

The following examples are offered to illustrate, but not to limit the claimed invention.

Example 1

Figure 1:
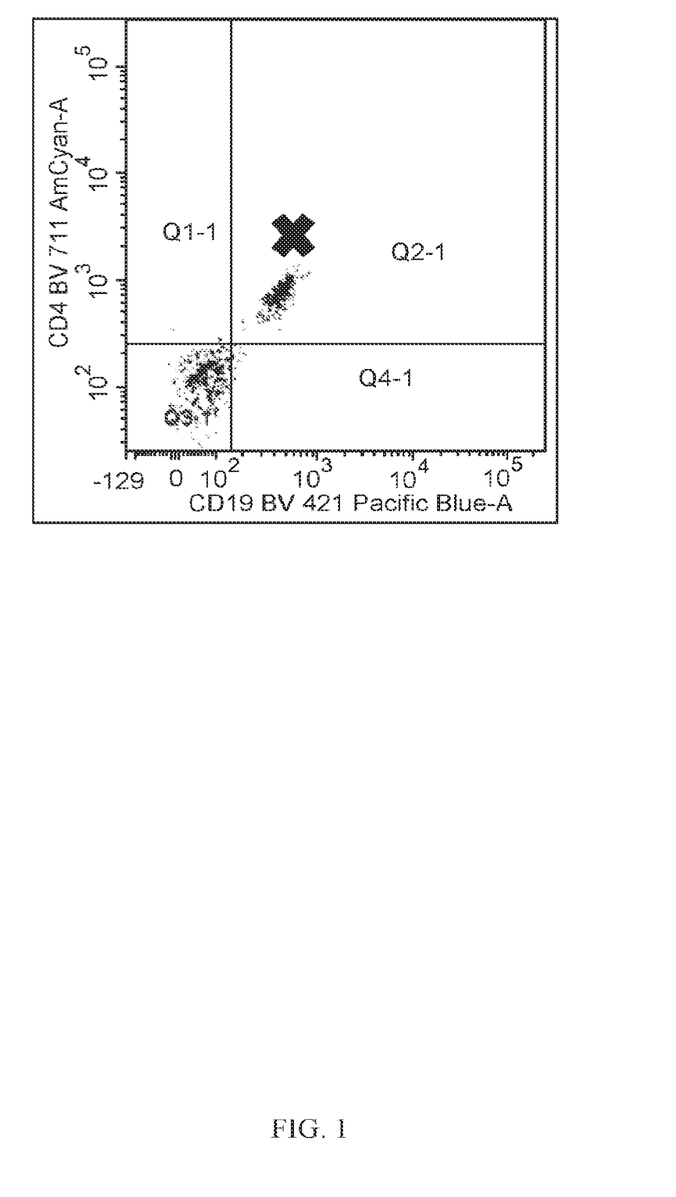
FIG. 1 illustrates that polymeric dyes interact with each other, causing the flow cytometer to display anomalous cell populations that cannot exist in reality. The histogram from dried BV dyes (CD19-BV 421 & CD4-BV711) showed anomalous population in Q2. This occurs consistently after dry down indicating an interaction of the polymeric dyes during drying process.

This experiment demonstrates that drying a cocktail comprising multiple labeled binding partners produce false results, which is caused by non-specific attachment between the labeled binding partners. A cocktail comprising two labeled binding partners was dried down in a standard 12×75 tube: anti-CD19 antibody conjugated with Brilliant Violet (BV) 421 (BD Biosciences), and anti-CD4 antibody conjugated with BV 711 (BD Biosciences). A blood sample was added to the tube. After a period of time sufficient for the dissolving the dried antibody-BV conjugates and labeling of the cells with these conjugates, the labeled cells were then subject to flow cytometry analysis. The results, shown in FIG. 1, showed an anomalous cell population that is both CD19 and CD4 positive. Since the majority of lymphocytes are either T cells, which express CD4 but not CD19; or B cells, which express CD19 but not CD4, a result showing a significant number of cells positive for both CD19 and CD4 is most likely due to the fact that two antibody-BV conjugates non-specifically attached to each other and thus both bind to the same cell.

Example 2

This experiment demonstrates that a labeled binding partner can be dried down and then reconstituted and the reconstituted labeled partner retained its binding activity to its target analyte.

Figure 2:
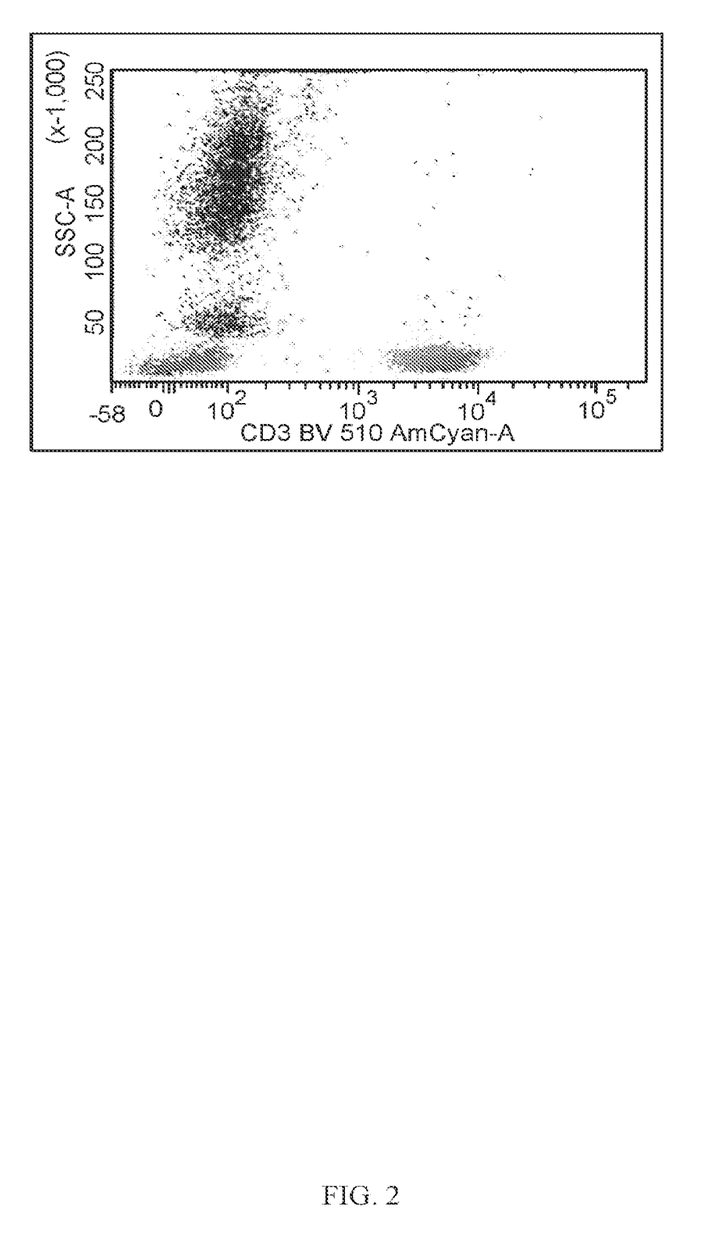
FIG. 2 shows the flow cytometry results using an antigen-antibody conjugate, which was dried down and then reconstituted before applied to the sample.

A labeled binding partner, an AmCyan-conjugated anti-CD3 antibody, was dispensed on a membrane, e.g., nitrocellulose or cellulose acetate, and dried down. The membrane was then placed in a standard 12×75 tube. A blood sample was added to the tube. After a period of time sufficient for the reconstitution and binding of the binding partners to the target analyte, the labeled blood cells are subject to flow cytometry analysis. The results showed a population of cells positive for CD3, indicating the reconstituted antibody-dye conjugate retained its binding activity to the CD3 marker expressed in T lymphocytes in the blood sample. See FIG. 2.

Example 3

This experiment demonstrates that drying two labeled binding partners at different locations eliminated false double positive cell population.

Figure 3A:
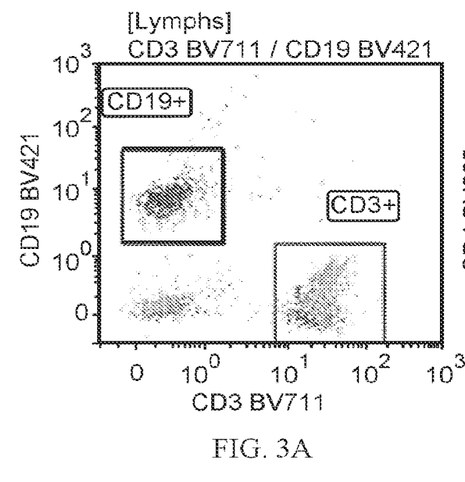
FIGS. 3A-3C show the flow cytometry results using two antigen-antibody conjugates. The conjugates were dried down on the same membrane, but at different locations, before applied to the sample.
Figure 3B:
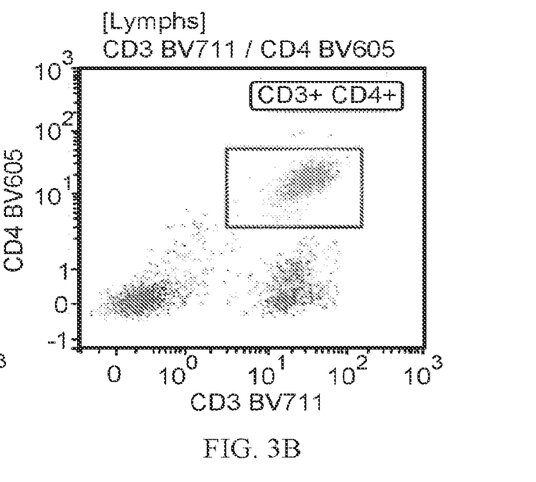
Figure 3C:
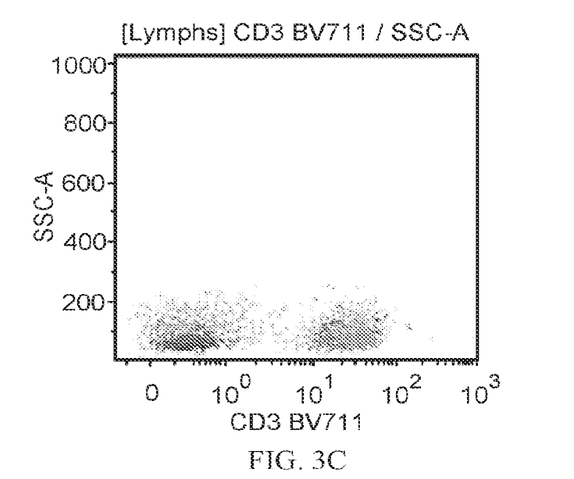

Two labeled binding partners, a BV711-conjugated anti-CD3 antibody and a BV421-conjugated anti-CD19 antibody, were dried down on different locations on the same membrane, nitrocellulose or cellulose acetate. The membranes having the dry, labeled binding partners were attached to the surface of a standard 12×75 tube. A blood sample was added to the tube. After a period of time sufficient for the reconstitution and binding of the binding partners to the target analyte, the labeled cells are subject to flow cytometry analysis. The results showed a CD19 positive, a CD3 positive, a double positive (positive for both CD3 and CD4) population, indicating the presence of B cell, T cells, and CD4 T cells, respectively. FIGS. 3A and 3B. The percentage of each cell population was consistent with their representation in blood. In FIG. 3A, the percentage of various labeled cell populations are shown in Table 1. There were no false, double positive cells—cells positive for both CD 19 and CD 3—when stained with both a BV711-conjugated anti-CD3 antibody and a BV421-conjugated anti-CD19 antibody. This indicates drying the labeled binding partners on different locations on the same substrate solved the problem of having false double positive results. FIG. 3C shows the CD3 positive cells when stained with a single labeled binding partner: the BV711-conjugated anti-CD3 antibody.

TABLE 1

Percentages of labeled cell populations

| Gate | % Gated | X-Med | Y-Med |
|---|---|---|---|
| All | 100.00 | 18.18 | 0.27 |
| CD19+ | 20.67 | 0.37 | 7.43 |
| CD3+ | 62.16 | 27.04 | 0.21 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A reaction vessel comprising:
   a first dry reactant spot disposed on a first membrane substrate, wherein the first membrane substrate is attached to an inside surface of the body of the reaction vessel, the first dry reactant spot comprising a first binding partner conjugated to a first dye; and
   a second dry reactant spot disposed on a substrate selected from the group consisting of the first membrane substrate, a second membrane substrate, a bead, and an inside surface of the reaction vessel, the second dry reactant spot comprising a second binding partner conjugated to a second dye;
   wherein the first dry reactant spot and the second dry reactant spot do not overlap; and
   wherein the reaction vessel is configured to receive a liquid sample that is capable of forming a liquid reaction mixture comprising the first binding partner and the second binding partner in the reaction vessel.

2. The reaction vessel of claim 1, further comprising a divider disposed between the first dry reactant spot and the second dry reactant spot.

3. The reaction vessel of claim 2, wherein the divider is configured to separate the first binding partner from the second binding partner in the reaction vessel before receiving the liquid sample.

4. The reaction vessel of claim 1, wherein the second dry reactant spot is disposed on a bead substrate.

5. The reaction vessel of claim 1, wherein at least one of the first dye and the second dye is a polymer dye.

6. The reaction vessel of claim 1, wherein both of the first dry reactant spot and the second dry reactant spot are disposed on the first membrane substrate.

7. The reaction vessel of claim 1, wherein at least one of the first dry reactant spot and the second dry reactant spot is in the form of a film.

8. The reaction vessel of claim 1, wherein the first binding partner conjugated to the first dye in the first spot and the second binding partner conjugated to the second dye in the second spot are stable at room temperature for at least one month, or at least one year.

9. The reaction vessel of claim 1, wherein the reaction vessel is selected from the group consisting of a tube, a plate, a well of a microtiter plate, a chamber, and a slide.

10. A method of preparing two or more dry reactant spots for use with a liquid sample, the method comprising:
    drying a first reactant in liquid phase onto a first membrane substrate to form a first dry reactant spot, the first reactant comprising a first binding partner conjugated to a first dye; and
    drying a second reactant in liquid phase onto a substrate selected from the group consisting of the first membrane substrate, a second membrane substrate, a bead, and an inside surface of the reaction vessel to form a second dry reactant spot, the second reactant comprising a second binding partner conjugated to a second dye, wherein at least one of the first dye and second dye is a polymer dye, wherein the first dry reactant spot and the second dry reactant spot do not overlap, and wherein the first dry reactant spot and second dry reactant spot are capable of forming a liquid reaction mixture comprising the first binding partner and the second binding partner when contacted with the liquid sample; and
    placing the first membrane substrate inside a reaction vessel.

11. The method of claim 10, further comprising maintaining physical separation of the first reactant and the second reactant during drying.

12. The method of claim 10, wherein the drying of the second reactant in liquid phase is onto the first membrane substrate.

13. The method of claim 10, further comprising bonding the first membrane substrate to an inside surface of a the reaction vessel.

14. The method of claim 10, wherein the drying of the second reactant in liquid phase is onto a bead substate.

15. The reaction vessel according to claim 1, wherein the at least one of the first or second membrane substrate(s) is selected from the group consisting of plastic, nitrocellulose, cellulose acetate, and glass.

16. The reaction vessel according to claim 1, wherein at least one of the first dye and the second dye is a monomeric dye.

17. The reaction vessel of claim 7, wherein at least one of the first dry reactant spot film and the second dry reactant spot film further comprises a stabilizer.

18. The method of claim 10, wherein at least one of the liquid phase of the first reactant and the liquid phase of the second reactant further comprises a stabilizer.

19. The reaction vessel of claim 1, wherein the second dry reactant spot is disposed on a second membrane substrate.

20. The reaction vessel of claim 1, wherein the second dry reactant spot is disposed on an inside surface of the reaction vessel.

* * * * *